United States Patent
Helfenbein et al.

(10) Patent No.: US 9,445,738 B2
(45) Date of Patent: Sep. 20, 2016

(54) RESPIRATION-GATED CARDIOGRAPHY

(75) Inventors: Eric D. Helfenbein, Sunnyvale, CA (US); A. Dean Forbes, Palo Alto, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 2444 days.

(21) Appl. No.: 12/293,552

(22) PCT Filed: Mar. 5, 2007

(86) PCT No.: PCT/US2007/063274
§ 371 (c)(1),
(2), (4) Date: Sep. 19, 2008

(87) PCT Pub. No.: WO2007/109406
PCT Pub. Date: Sep. 27, 2007

(65) Prior Publication Data
US 2011/0190647 A1 Aug. 4, 2011

Related U.S. Application Data

(60) Provisional application No. 60/784,830, filed on Mar. 22, 2006.

(51) Int. Cl.
*A61B 5/0402* (2006.01)
*A61B 5/0452* (2006.01)
*A61B 5/00* (2006.01)
*A61B 5/08* (2006.01)

(52) U.S. Cl.
CPC ............ *A61B 5/0452* (2013.01); *A61B 5/721* (2013.01); *A61B 5/7285* (2013.01); *A61B 5/0809* (2013.01); *A61B 5/7289* (2013.01); *A61B 5/7292* (2013.01)

(58) Field of Classification Search
USPC ................. 600/508–509, 513, 529, 532
See application file for complete search history.

(56) References Cited

U.S. PATENT DOCUMENTS

| | | |
|---|---|---|
| 4,893,630 A | 1/1990 | Bray |
| 5,025,784 A | 6/1991 | Shao et al. |
| 5,148,812 A | 9/1992 | Verrier et al. |
| 5,188,116 A | 2/1993 | Pommrehn et al. |
| 5,511,554 A | 4/1996 | Helfenbein et al. |
| 5,842,989 A | 12/1998 | Zur |
| 6,132,381 A | 10/2000 | Forbes et al. |
| 6,169,919 B1 | 1/2001 | Nearing et al. |
| 6,415,174 B1 | 7/2002 | Bebehani et al. |
| 7,447,543 B2 | 11/2008 | Belalcazar et al. |
| 2004/0254481 A1* | 12/2004 | Brodnick ............... 600/484 |

FOREIGN PATENT DOCUMENTS

WO 9520351 A1 8/1995

\* cited by examiner

*Primary Examiner* — Deborah Malamud

(57) ABSTRACT

In a cardiographic apparatus (10), a plurality of electrodes (16) are configured for operative connection with a subject (14). A cardiograph (12, 12', 12') is connected with the plurality of electrodes to acquire cardiographic data. A respiratory gate (20, 22, 26, 36, 46, 50, 52, 54) is configured to identify end expiration periods or other quiescent respiratory periods so as to generate a cardiographic dataset (30) limited to the identified end-expiration periods from cardiographic data acquired by the cardiograph at least during the identified end expiration periods.

19 Claims, 4 Drawing Sheets

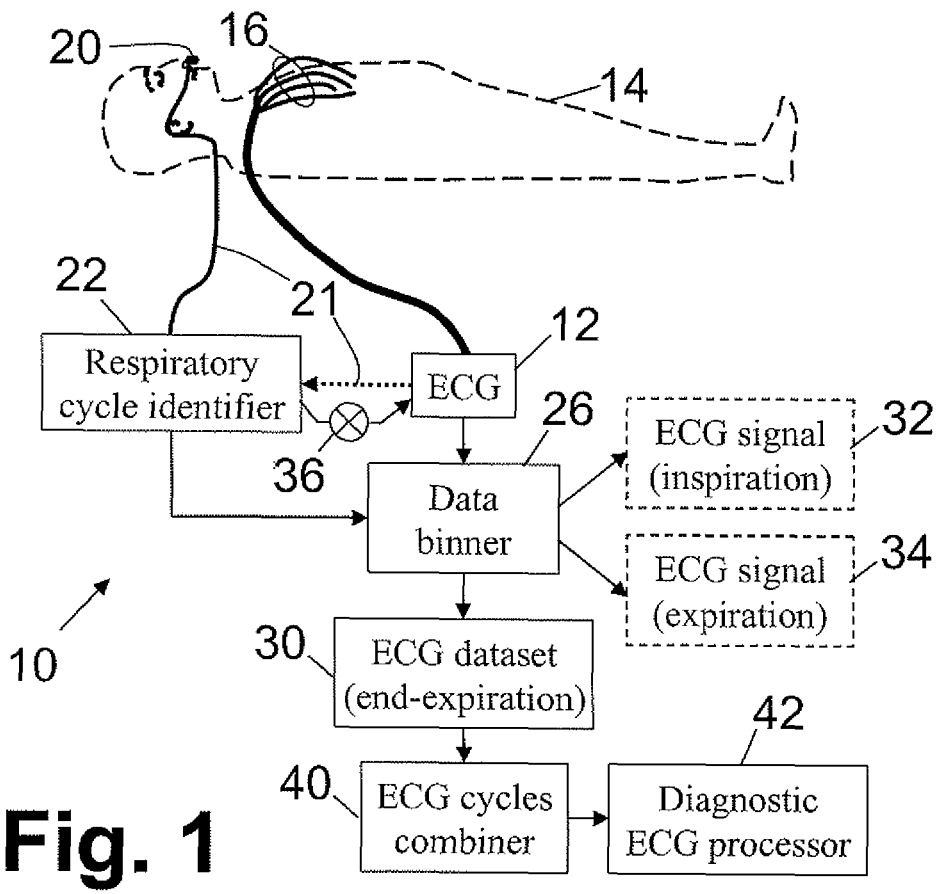
Fig. 1
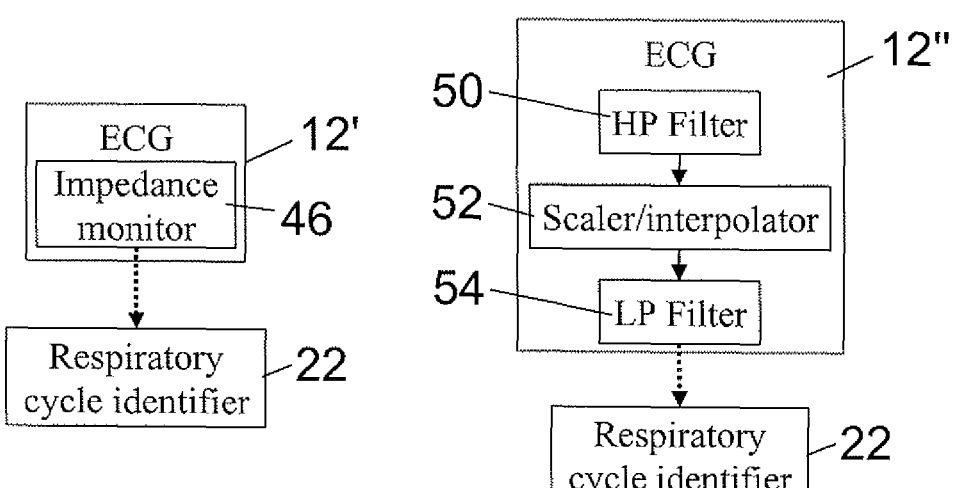
Fig. 2
Fig. 3

RESPIRATION-GATED CARDIOGRAPHY

CROSS REFERENCE TO RELATED APPLICATIONS

This application claims the benefit of U.S. provisional application Ser. No. 60/784,830 filed Mar. 22, 2006, which is incorporated herein by reference.

The following relates to the medical monitoring arts. It finds particular application in conjunction with electrocardiograph (ECG) equipment and electrocardiographic monitoring of patients for diagnostic analysis, and will be described with particular reference thereto. However, the following is also applicable to electrocardiographic monitoring in general, such as during routine medical checkups, as part of in-hospital patient monitoring, and so forth.

Existing automated electrocardiographic analysis algorithms in diagnostic electrocardiography typically use all beats in a standard 10-second recording using a standard 12-lead ECG setup to form representative beat waveforms. For a typical pulse rate of 60-90 beats per minute, a ten-second interval provides about 10-15 electrocardiographic cycles (corresponding to 10-15 heartbeats). The acquired 10-15 electrocardiographic cycles are averaged, for example by temporally shifting the electrocardiographic cycles to register or align the R-wave peak or one or more other features of the electrocardiographic cycle, and averaging or median filtering the registered electrocardiographic cycles. Measurements of key time intervals, voltages, and so forth which are used for medical diagnoses are made on the averaged data.

Averaging or median filtering enables reduction in noise due to muscle tremors, patient breathing, or other motion artifacts, as well as reducing electromagnetic interference (EMI) noise such as 60 Hz and 180 Hz power line noise. Including 10-15 electrocardiographic cycles over the conventional 10-second period has generally been considered to provide sufficient noise reduction, but in fact noise has still been found to be problematic even after averaging or filtering, and consistent results from consecutive tests are not always obtained. To provide more noise suppression, the skilled artisan sometimes averages additional electrocardiographic cycles acquired over a time period greater than ten seconds. This approach is sometimes used, for example, in intensive care or other settings where continuous electrocardiographic monitoring is performed. Another known approach for improving consistency between electrocardiographic cycles is to normalize the amplitude of the R-wave or other electrocardiographic feature prior to averaging. However, this approach distorts the data and adversely affects diagnostic analyses.

While existing averaging and/or normalization techniques provide substantial noise reduction, it is known in the art that noise remaining after such averaging can still limit the accuracy reliability, and repeatability of medical diagnoses, health screenings, and other electrocardiographic monitoring.

The following contemplates improvements that overcome the aforementioned limitations and others.

According to one aspect, a cardiographic method is disclosed, including: determining a respiratory waveform correlating with respiration occurring during acquiring of the cardiographic data; and generating a cardiographic dataset from one or more portions of the acquired cardiographic data corresponding to one or more substantially quiescent portions of the respiratory cycle identified using the respiratory waveform.

According to another aspect, an electrocardiographic apparatus is disclosed which includes means for acquiring electrocardiographic data; determining one or more end-expiration periods of the respiratory cycle occurring during the acquiring of the electrocardiographic data; and generating an electrocardiographic dataset from electrocardiographic data acquired during the one or more end-expiration periods of the respiratory cycle.

According to another aspect, a cardiographic apparatus is disclosed. A plurality of electrodes are configured for operative connection with a subject. A cardiograph is connected with the plurality of electrodes to acquire cardiographic data. A respiratory gate is configured to identify end-expiration periods so as to generate a cardiographic dataset limited to the identified end-expiration periods from cardiographic data acquired by the cardiograph at least during the identified end-expiration periods.

One advantage resides in reduced noise in electrocardiographic data without concomitant increase in electrocardiographic data acquisition time.

Another advantage resides in reduced respiration-related electrocardiographic monitoring noise.

Another advantage resides in reduced muscle motion-related electrocardiographic monitoring noise.

Another advantage resides in enhanced reliability of medical diagnoses, health screenings, and so forth based on electrocardiographic data.

Another advantage resides in improved consistency in electrocardiographic data.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a cardiographic apparatus including respiratory gating.

FIG. 2 diagrammatically shows one ECG-based respiration monitoring approach suitably used in the cardiographic apparatus of FIG. 1.

FIG. 3 diagrammatically shows another ECG-based respiration monitoring approach suitably used in the cardiographic apparatus of FIG. 1.

FIG. 4 plots electrocardiographic data (top, using Lead X) versus a respiratory waveform (bottom) acquired using the impedance monitor of FIG. 2.

Figure 6:
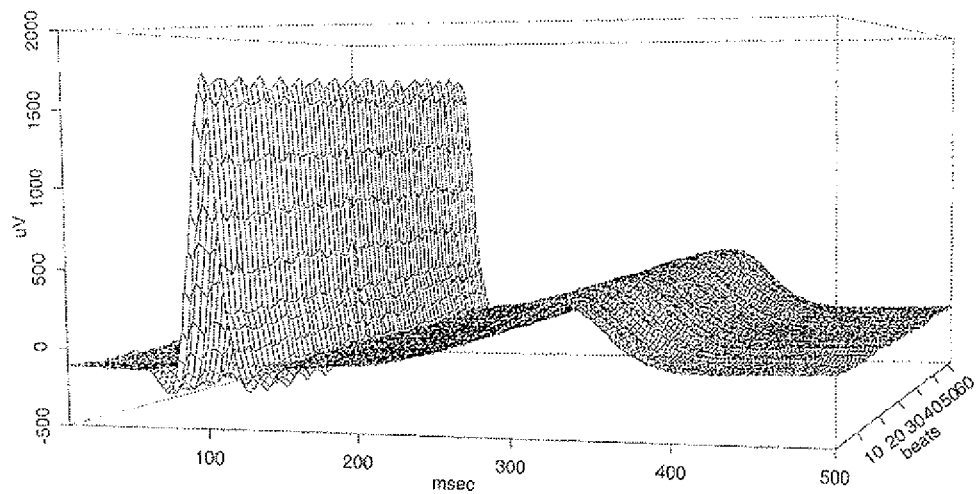
FIG. 6 shows a three-dimensional plot of electrocardiographic cycles aligned at the start of depolarization (QRS onset) without respiratory gating.
Figure 8:
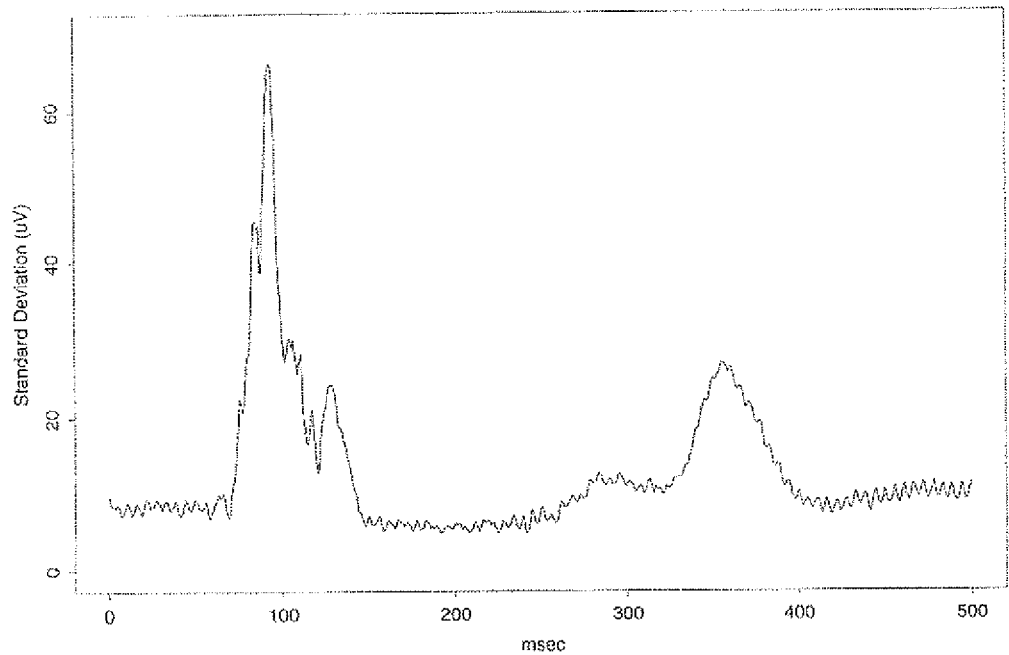

FIG. 8 plots standard deviation of the electrocardiographic cycles of FIG. 6.

Figure 7:
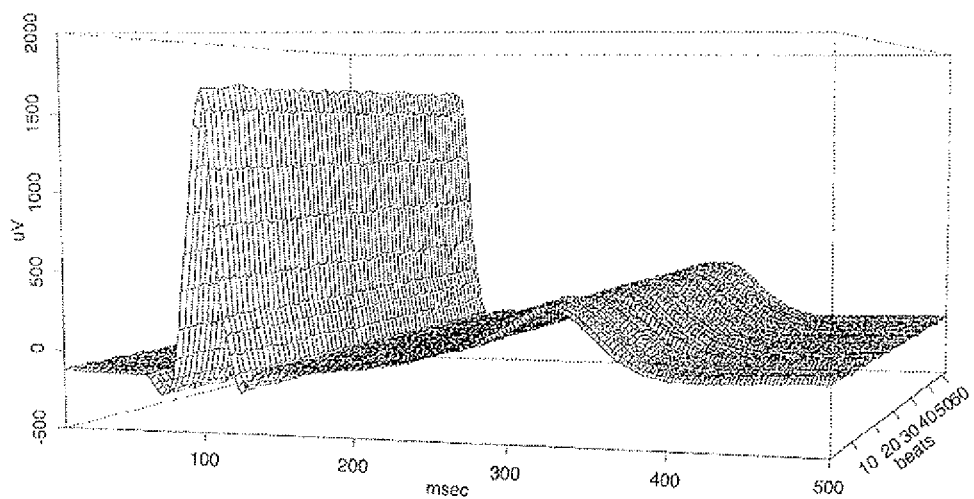
FIG. 7 shows a three-dimensional plot of successive electrocardiographic cycles aligned at the start of depolarization (QRS onset) with respiratory gating, such that only electrocardiographic cycles acquired during the end-respiration period are included.
Figure 9:
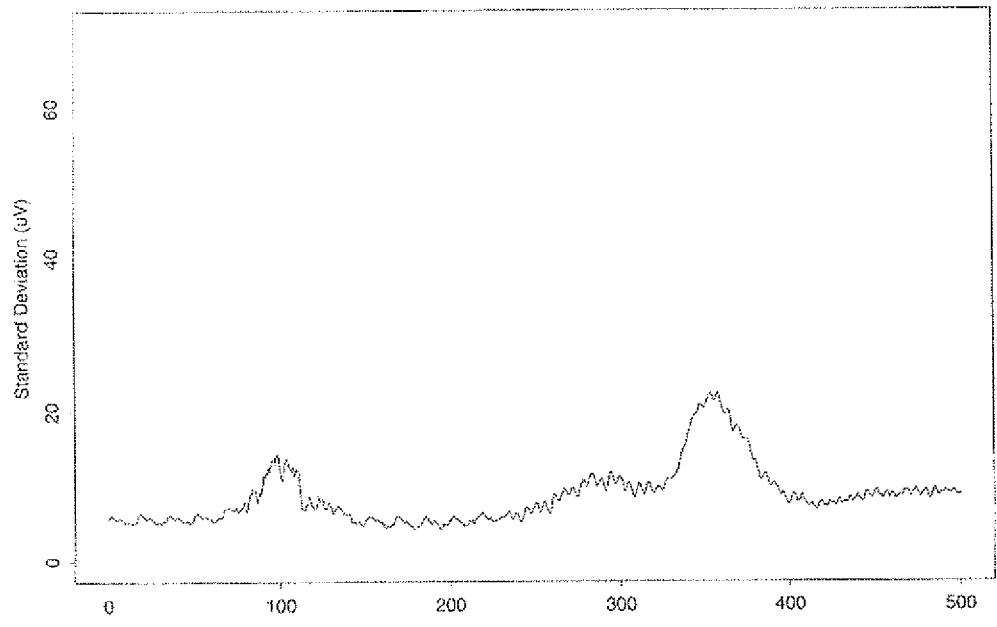

FIG. 9 plots standard deviation of the respiration-gated electrocardiographic cycles of FIG. 7.

With reference to FIG. 1, a cardiographic apparatus 10 includes a cardiograph, such as an illustrated electrocardiograph (ECG) 12, or an impedance cardiograph, or so forth, connected to a patient 14 (shown in phantom to indicate that the patient is not a component of the cardiographic apparatus 10) or other subject by a plurality of electrodes 16. The illustrated electrodes 16 are drawn diagrammatically. The electrodes 16 in some embodiments conform with a typical 12-lead ECG setup in which two electrodes connect with the patient's arms or hands, two electrodes connect with the patient's legs or feet, an electrode conventionally denoted "V1" connects just to the right of the breastbone, an electrode "V2" connects just to the left of the breastbone, and additional electrodes "V3", "V4", "V5", and "VG" connect left of the breastbone at successively greater distances from the breastbone. The example ECG signals described and illustrated herein were acquired using the conventional 10-electrode, 12-lead ECG setup known to the art. However, the respiratory-gated electrocardiographic techniques and apparatuses disclosed herein are suitably practiced with other ECG lead setups, including ECG lead setups employing fewer or more than 12 leads, such as a 3-lead ECG setup, ECG lead setups including leads connected in different configurations to the chest and/or selected limbs and/or including electrodes connected to body parts other than the chest and limbs, and so forth.

With continuing reference to FIG. 1, in some embodiments a respiratory monitor 20 generates a respiratory waveform 21 (diagrammatically indicated in FIG. 1 by a signal line extending from the respiratory monitor 20 representative of a wired connection, although a wireless output is also contemplated for the respiratory monitor) correlating with respiration occurring during electrocardiographic data acquisition. Some suitable respiratory monitors include, for example, an illustrated nasal flow sensor 20, or a plesthsygmograph measuring air flow of the lungs, or a mechanical strain gauge measuring chest expansion, or another respiratory monitor measuring airflow of the lungs, chest movement, or another biometric parameter correlating with respiration. Such a respiratory monitor 20 is suitably operatively independent of the ECG 12. As will be discussed in more detail with reference to FIGS. 2 and 3, in some embodiments the respiratory waveform 21 is generated from the electrocardiographic data itself, or from impedance measurements across selected leads of the plurality of leads 16 connected with the ECG 12. (The respiratory waveform 21 for these embodiments is diagrammatically indicated in FIG. 1 by a dotted line extending from the ECG 12, although it is to be understood that the respiratory waveform output by or associated with the ECG 12 is optionally a wireless output). A respiratory cycle identifier 22 monitors the respiratory waveform 21 output by the respiratory monitor 20 or output by or associated with the ECG 14 or leads 16, to determine one or more substantially quiescent portions of the respiratory cycle. During such quiescent portions, the lungs are preferably substantially at rest or inactive, so that chest movement is reduced to provide more consistent electocardiographic data.

In the embodiments illustrated herein, the quiescent portion employed for gating of electrocardiographic data is the end-expiration period of the respiratory cycle. Each end-expiration period is detectable in the respiratory waveform 21, and is temporally preceded by an expiration period of the respiratory waveform 21 and temporally succeeded by an inspiration period of the respiratory waveform 21. In other words, the end-expiration period corresponds about to the quiescent period between completion of exhalation of one breath and initiation of inhalation of the next breath. The inventors have found that the end-expiration period has substantial advantages for gating of electrocardiographic data collection. The end-expiration period is relatively long, typically spanning about two-thirds of the respiratory cycle for rest breathing and about one-half of the respiratory cycle for heavier breathing. Additionally, the inventors have observed substantial consistency of electrocardiographic cycles (corresponding to cardiac cycles) acquired during end-expiration, even across several breaths.

Without being limited to any particular theory of operation, it is believed that heartbeats occurring during end-expiration form a stable beat morphology or shape with substantially reduced respiration-induced axis shift due to translation and/or rotation of the heart within the chest cavity, the consistent positional relationship of the heart and the ECG electrodes, and with substantially reduced high-frequency muscle-artifact noise due to electrical activation of the chest muscles and diaphragm. Accordingly, electrocardiographic cycles acquired during the end-expiration period are more repeatable and more precisely measurable than electrocardiographic cycles acquired during other phases or periods of respiration.

Although the end-expiration period has been found to be an appropriate quiescent respiratory period for gating electrocardiographic data, it is also contemplated to employ other quiescent periods of the respiratory cycle for gating electrocardiographic data, such as the end-inspiration period disposed between completion of inspiration and initiation of expiration. The end-inspiration period is expected to exhibit more respiration-induced axis shift of the heart due to the expanded lungs, as compared with the end-expiration period during which the lungs contain less air. Moreover, the end-inspiration period is typically shorter in duration than the end-expiration period. However, the end-inspiration period is advantageously also expected to be substantially quiescent in that the heart is not undergoing substantial respiration-induced translation or rotation during end-inspiration.

The respiratory cycle identifier 22 monitors the respiratory waveform 21 to determine one or more substantially quiescent portions of the respiratory cycle, such as one or more end-expiration periods. This information is used by a data binner 26 to generate an electrocardiographic dataset 30 from one or more portions of the acquired electrocardiographic data corresponding to the one or more substantially quiescent portions of the respiratory cycle. Optionally, the data binner 26 also bins electrocardiographic data from other periods of the respiratory cycle based on the respiratory waveform 21, such as electrocardiographic data acquired during the inspiration period 32, electrocardiographic data acquired during the expiration period 34, or so forth. The data binner 26 provides retrospective respiration-based gating of the electrocardiographic data, in which electrocardiographic data is acquired continuously by the ECG 12, and the electrocardiographic dataset 30 is generated as one or more portions of the continuously acquired electrocardiographic data acquired during the identified one or more substantially quiescent portions of the respiratory cycle.

Alternatively, a prospective gating approach can be used. In prospective approaches, the ECG 12 does not operate continuously, but rather is controlled by the respiratory cycle identifier 22, which operates in real-time (or substantially in real-time) to monitor the respiratory waveform 21 to detect onset of the end-expiration period. Upon such detection, the respiratory cycle identifier 22 operates a controller 36 to start acquisition of electrocardiographic data. The respiratory cycle identifier 22 continues to monitor the respiratory waveform 21 during the end-expiration period so as to detect onset of the succeeding inspiration period. When inspiration onset is detected, the respiratory cycle identifier 22 operates the controller 36 to stop acquisition of electrocardiographic data. In this way, the controller 36 causes the ECG 12 to acquire electrocardiographic data only during the identified end-expiration periods, so that the acquired electrocardiographic data defines the electrocardiographic dataset 30 limited to the end-expiration period or periods.

In some embodiments, the resulting electrocardiographic dataset 30 includes a plurality of electrocardiographic cycles. For example, in a standard 10-second 12-lead ECG acquisition about 10-15 electrocardiographic cycles are typically acquired. If the resting end-respiration period is about two-thirds of the total respiration cycle, then the electrocardiographic dataset 30 limited to the end-expiration periods will include about 6-10 electrocardiographic cycles. Conversely, sampling can be extended until a fixed number of cycles, e.g., 15, are acquired, which lengthens the measurement period from 10 to about 15 seconds. In such a case, the electrocardiographic cycles of the electrocardiographic dataset 30 are optionally combined by an electrocardiographic cycles combiner 40 to produce a representative electrocardiographic cycle. Such combining can be performed, for example, by registering the electrocardiographic cycles temporally (for example, to align the temporal occurrences of the R-wave peaks) and averaging the several signals at each point along the electrocardiographic cycle. The combining optionally includes interpolation, smoothing, or other signal processing. Moreover, rather than combining by averaging, the combining can involve median filtering or other combinatory formulation.

The representative electrocardiographic cycle produced by the electrocardiographic cycles combiner 40 are optionally processed by a diagnostic ECG processor 42, which may for example extract quantitative measures of time intervals or durations, signal amplitudes, peak areas or morphologies, or other quantitative measures suitable for use in diagnostic analysis. Some example quantitative measures may include: the time interval occupied by the QRS-complex; the amplitude of the P-wave, the amplitude of the R-wave, the amplitude of the T-wave, the QRS-complex area; the T-wave area; and so forth. The inventors have found that the accuracy and consistency of such quantitative measurements, especially during the QRS complex, is substantially improved when the representative electrocardiographic cycle is constructed by combining only electrocardiographic cycles acquired during the end-expiration period.

With continuing reference to FIG. 1 and with further reference to FIG. 2, an embodiment of the ECG 12' is illustrated that includes an impedance monitor 46 to monitor impedance between selected electrodes of the plurality of electrodes 16 to generate the respiratory waveform 21. As the lungs fill with air, the electrical impedance across the thorax changes. The respiratory waveform 21 is obtained by measuring impedance across a selected pair of electrodes of the plurality of electrodes 16 attached to the chest or limbs of the patient 14. Advantageously, this respiratory monitoring technique employs no additional sensors or connections to the patient 14 other than the electrodes 16 employed for electrocardiographic data acquisition. The ECG 12' includes the impedance measuring hardware 46 in addition to typical electrocardiographic data acquisition electronics. The PageWriter Trim cardiograph (available from Philips Medical Systems, Eindhoven, Netherlands) employs a signal acquisition chip that includes the capability to measure impedance between electrodes—accordingly, modifying such an existing ECG to include the impedance monitor 46 is straightforward.

With continuing reference to FIG. 1 and with further reference to FIG. 3, an embodiment of the ECG 12" is illustrated that includes signal processing components 50, 52, 54 for extracting the respiratory waveform 21 from the electrocardiographic data. The illustrated embodiment employs signal processing disclosed in detail in U.S. Pat. No. 5,913,308. This approach for generating the respiratory waveform 21 takes advantage of the following physiological phenomenon. As the intercostal chest muscles are activated during respiration, the muscle activity is typically picked up as high-frequency muscle artifacts or oscillations that are superimposed on the electrocardiac signal. The energy of the muscle artifact is correlated with the phases or periods of the respiration cycle. In the ECG 12", a high-pass filter 50 at least partially isolates the high-frequency muscle tremor from the lower frequency components of the electrocardiographic signal. The high-pass filter 50 removes the low-frequency and DC components of the electrocardiographic signal. In a suitable approach, the high-pass filter 50 is a finite impulse response (FIR) high-pass filter having a cutoff of 250 Hz which is suitable for processing electrocardiographic data sampled at 2000 samples per second. Optionally, scaler/interpolator circuitry 52 processes the high-pass filtered data to further remove components unrelated to muscle artifacts or oscillations. For example, the scaler/interpolator circuitry 52 optionally smooths or interpolates across the QRS-complex to further suppress features related to cardiac cycling. A low-pass filter 54 is optionally applied to smooth the high-pass filtered and optionally scaled or interpolated signal so as to produce the respiratory waveform 21 primarily including muscle artifacts or oscillations associated with respiration. One example of a suitable low-pass filter is the physiological event time averaging (PETA) filter described in U.S. Pat. No. 5,511,554. It is to be appreciated that the described signal processing components 50, 52, 54 for extracting the respiratory waveform 21 from the electrocardiographic data are examples, and that other arrangements or configurations of signal processing may be used to extract the respiratory waveform 21.

In FIGS. 2 and 3, the ECG 12' and ECG 12" each include the components 46, 50, 52, 54 for generating the respiratory waveform 21 integral with the ECG. However, in other embodiments some or all such components may be external to the ECG, for example interposed between the ECG and the respiratory cycle identifier 22 and/or integrated with the respiratory cycle identifier 22.

With reference to FIGS. 4-9, some illustrative experimental results are now described. The electrocardiographic data were acquired using a 12-lead electrocardiographic setup for the electrodes 16. Respiratory waveforms 21 were generated by the impedance monitor 46 of FIG. 2 coupled with PETA filtering as described in U.S. Pat. No. 5,511,554 to remove effects of cardiac pumping and to generate a smoothed respiratory waveform 21. These results show that a substantial portion of ECG "noise" is due to the major effect that breathing has on the electrocardiogram. During the respiratory cycle, muscle-artifact noise due to electrical activation of the chest muscles and diaphragm is super-imposed onto the electrocardiographic signal, especially during inspiration. Also, as a subject breathes, the heart lifts and rotates within the chest cavity during each breathing cycle, and thus moves in space relative to recording electrodes placed on the chest surface. Thus, individual heartbeat waveforms recorded in a fixed recording lead represent "snapshots" of the heart taken when the heart is in different positions. There is a significant amount of beat-to-beat variation and axis shift in the waveforms that is due solely to this breathing effect. When these snapshots are averaged together, the effects of breathing are not accounted for, and the result can be thought of as a "blurred" image. This effect plays a key role in test consistency, in that consecutively repeated tests may produce differing results. Accordingly, improved methods and apparatuses providing further noise reduction by addressing the effects of respiration in electrocardiographic monitoring are desirable.

Figure 4:
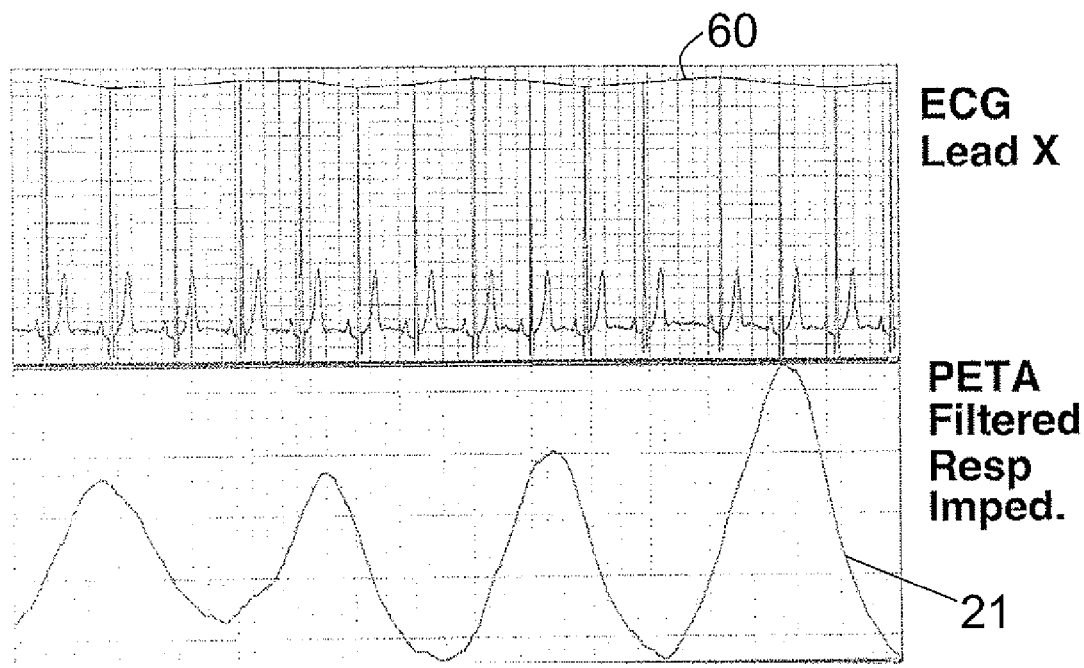

FIG. 4 plots electrocardiographic data (top, using Lead X) versus a respiratory waveform 21 (bottom). In FIG. 4, an interpolation 60 of the R-wave peak is drawn in to demonstrate the extent to which variations in the electrocardiographic data correlate with the respiratory waveform 21.

Figure 5:
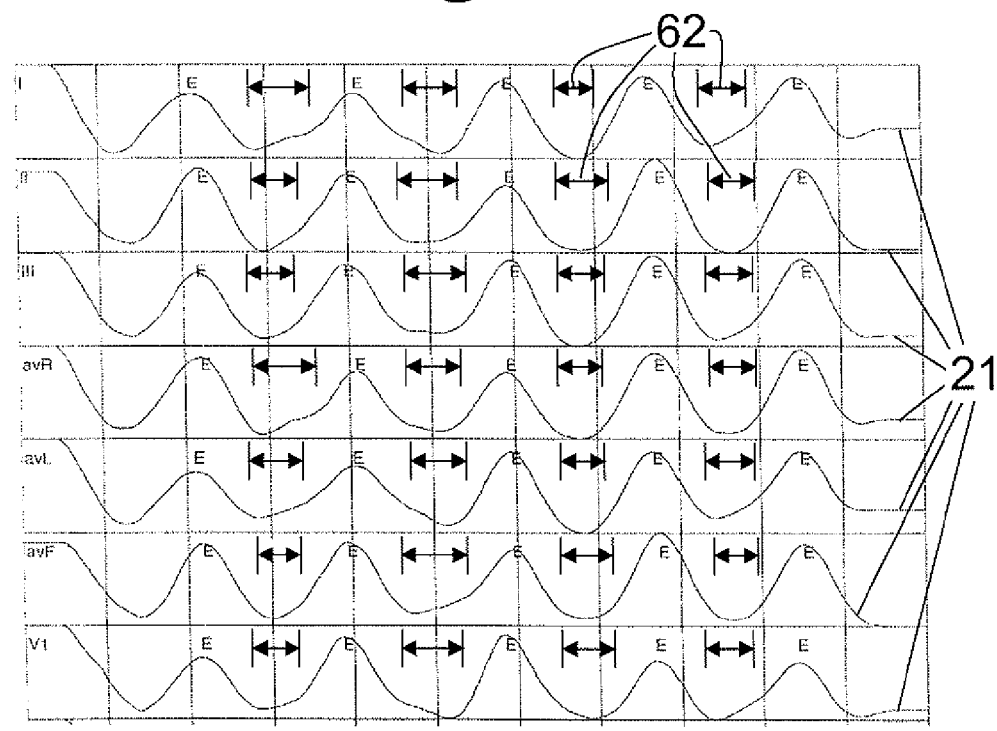
FIG. 5 shows temporally aligned respiratory waveforms acquired using the impedance monitor of FIG. 2 applied to Lead I, Lead II, Lead III, Lead aVR, Lead aVL, lead aVF, and lead V1 of a conventional 12-lead ECG setup. The letters "E" in FIG. 5 indicate beginning of the expiration period, while the double-arrowhead time intervals indicate the determined end-expiration periods.

FIG. 5 shows temporally aligned respiratory waveforms 21 acquired using the impedance monitor of FIG. 2 applied to Lead I, Lead II, Lead III, Lead aVR, Lead aVL, lead aVF, and lead V1 of the conventional 12-lead ECG setup. The letters "E" in FIG. 5 indicate beginning of the expiration period, while the double-arrowhead time interval indicators 62 indicate the end-expiration periods determined by the respiratory cycle identifier 22. The onset and termination of each end-expiration period can be determined from the respiratory waveform 21, for example based on inflection points in the respiratory waveform 21. FIG. 5 shows that the end-expiration period is typically a substantial fraction (e.g., about one-half to two-thirds) of the total respiratory cycle, ensuring that a substantial number of electrocardiographic cycles are provided for a typical 10-second acquisition interval. Moreover, the position and duration of the end-expiration periods is not strongly dependent upon which leads are selected for the impedance measuring.

FIGS. 6 and 7 show three-dimensional plots of electrocardiographic cycles aligned at the start of depolarization (QRS onset) without (FIG. 6) and with (FIG. 7) respiratory gating. A higher variability in the electrocardiographic data is seen between cycles in the ungated data of FIG. 6. In other words, the gated electrocardiographic data of FIG. 7 shows substantially improved consistency compared with the ungated electrocardiographic data of FIG. 6.

FIGS. 8 and 9 plots standard deviation of the electrocardiographic cycles of FIGS. 6 and 7, respectively. The standard deviation for the gated electrocardiographic cycles of FIG. 7 is substantially lower than the standard deviation for the ungated electrocardiographic cycles of FIG. 6. For the ungated electrocardiographic data of FIG. 6, a maximum variability of about 70 microvolts occurs at the R-wave peak. By comparison, the gated electrocardiographic data of FIG. 7 has a substantially lower maximum variability of about 20 microvolts.

In FIGS. 6-9 electrocardiographic data from a single lead of the 12-lead ECG setup are plotted. More generally, on each lead of the acquired 12-lead ECG setup the electrocardiographic data signals of those electrocardiographic cycles which are acquired during the end-expiration period are combined together (by averaging, median filtering, or other formulation) to obtain a representative electrocardiographic cycle for each lead. Measurements which are subsequently used for disease diagnoses are made on these representative beat complexes. If an ECG setup other than the conventional 12-lead ECG setup is employed, then similarly each lead of that ECG setup can be processed to produce a representative electrocardiographic cycle for that lead. Optionally, one or more of the acquisition channels may be unprocessed, for example if only certain available acquisition channels provide the quantitative information sought for diagnosis.

The illustrated embodiments relate to respiration-gated electrocardiography. However, it is also contemplated to employ the respiration-gating techniques disclosed herein in conjunction with other cardiography techniques, such as impedance cardiography in which impedance cardiographic data is acquired, rather than electrocardiographic data. Advantageously, impedance cardiographic data inherently provides impedance measurements between electrodes that can be used for determining the respiratory waveform analogously to the approach of FIG. 2.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A cardiographic apparatus comprising:
   a cardiograph configured for operative connection with a subject via a plurality of electrodes to acquire cardiographic data; and
   a respiratory gate configured for operative connection with the subject to (i) identify end-expiration periods which are quiescent periods between completion of exhalation of one breath and initiation of inhalation of the next breath and (ii) generate a cardiographic dataset limited to the identified end-expiration periods from cardiographic data acquired by the cardiograph at least during the identified end-expiration periods.

2. The cardiographic apparatus according to claim 1, wherein the respiratory gate includes:
   a signal processing component that receives cardiographic data acquired by the cardiograph and identifies end-expiration periods therefrom.

3. The cardiographic apparatus according to claim 1, wherein the respiratory gate includes:
   an impedance monitor that monitors impedance between selected electrodes of the plurality of electrodes and identifies end-expiration periods therefrom.

4. The cardiographic apparatus according to claim 1, wherein the respiratory gate includes:
   a respiratory monitor configured to monitor at least one of (i) airflow of the lungs and (ii) chest movement to identify end-expiration periods.

5. The cardiographic apparatus according to claim 4 wherein the respiratory gate comprises a nasal flow sensor, a plesthsygmograph, or a mechanical strain gauge.

6. The cardiographic apparatus according to claim 1, wherein the respiratory gate includes a controller causing that controls the cardiograph to acquire cardiographic data only during the identified end-expiration periods.

7. The cardiographic apparatus according to claim 1, further including:
   a respiration sensor that acquires respiration data concurrently with the acquiring of the cardiographic data and that is operatively independent of cardiographic electrodes used in the acquiring of the cardiographic data.

8. The cardiographic apparatus according to claim 1, wherein the cardiograph comprises:
   an electrocardiograph (ECG).

9. A cardiographic apparatus comprising:
- a cardiograph for connection with a plurality of electrodes to acquire cardiographic data; and
- a respiratory gate comprising a signal processing component configured to (i) identify end-expiration periods wherein each end-expiration period is temporally preceded by an expiration period and temporally succeeded by an inspiration period and (ii) generate a cardiographic dataset limited to the identified end-expiration periods from cardiographic data acquired by the cardiograph at least during the identified end expiration periods.

10. The cardiographic apparatus according to claim 9, wherein the respiratory gate includes:
- an impedance monitor that monitors impedance between selected electrodes of the plurality of electrodes and identifies end-expiration periods therefrom.

11. The cardiographic apparatus according to claim 9, wherein the respiratory gate includes:
- a respiratory monitor configured to monitor at least one of (i) airflow of the lungs and (ii) chest movement to identify end-expiration periods.

12. The cardiographic apparatus according to claim 11 wherein the respiratory gate comprises a nasal flow sensor, a plesthsygmograph, or a mechanical strain gauge.

13. The cardiographic apparatus according to claim 9, wherein the respiratory gate includes a controller causing that controls the cardiograph to acquire cardiographic data only during the identified end-expiration periods.

14. The cardiographic apparatus according to claim 9, further including:
- a respiration sensor that acquires respiration data concurrently with the acquiring of the cardiographic data and that is operatively independent of cardiographic electrodes used in the acquiring of the cardiographic data.

15. The cardiographic apparatus according to claim 9, wherein the cardiograph comprises:
- an electrocardiograph (ECG).

16. A cardiographic apparatus comprising:
- an electrocardiograph (ECG) configured for operative connection with a subject via a plurality of electrodes to acquire electrocardiographic data; and
- a respiratory gate including a respiratory monitor configured for operative connection with the subject to monitor at least one of airflow of the lungs and chest movement to (i) identify end-expiration periods which are quiescent periods between completion of exhalation of one breath and initiation of inhalation of the next breath and (ii) generate an electrocardiographic dataset limited to the identified end-expiration periods from electrocardiographic data acquired by the ECG at least during the identified end-expiration periods.

17. The cardiographic apparatus according to claim 16, wherein the respiratory monitor includes:
- an impedance monitor that monitors impedance between selected electrodes of the plurality of electrodes and identifies end-expiration periods therefrom.

18. The cardiographic apparatus according to claim 16, wherein the respiratory gate includes a controller that controls the ECG to acquire electrocardiographic data only during the identified end-expiration periods.

19. The cardiographic apparatus according to claim 16 wherein the respiratory monitor comprises a nasal flow sensor, a plesthsygmograph, or a mechanical strain gauge.

* * * * *